United States Patent [19]

Child et al.

[11] Patent Number: 4,900,756

[45] Date of Patent: Feb. 13, 1990

[54] (2,2-BIS(AMINOMETHYL)-1,3-PRO-PRANEDIOL-N,N')PLATINUM COMPLEXES

[75] Inventors: Ralph G. Child, Pearl River; Panayota Bitha, Pomona; Joseph J. Hlavka, Tuxedo; Yang-I Lin, Nanuet, all of N.Y.

[73] Assignee: American Cyanamid Company, Wayne, N.J.

[21] Appl. No.: 219,536

[22] Filed: Jul. 15, 1988

Related U.S. Application Data

[63] Continuation-in-part of Ser. No. 825,023, Jan. 31, 1986, Pat. No. 4,760,157.

[51] Int. Cl.$^4$ .................... A61K 31/28; A61K 31/66
[52] U.S. Cl. ..................... 514/492; 514/119
[58] Field of Search ................. 514/492, 119

[56] References Cited

U.S. PATENT DOCUMENTS

| | | | |
|---|---|---|---|
| 4,140,707 | 2/1979 | Clearg et al. | 556/137 |
| 4,410,544 | 10/1983 | Berg et al. | 556/137 |
| 4,431,666 | 2/1984 | Bueten et al. | 556/137 |
| 4,500,465 | 2/1985 | Amuwdsew et al. | 556/137 X |
| 4,587,331 | 5/1986 | Hlavka et al. | 556/137 X |

FOREIGN PATENT DOCUMENTS

| | | | |
|---|---|---|---|
| 2019399 | 10/1979 | United Kingdom | 556/137 |
| 2128615 | 5/1984 | United Kingdom | 556/137 |

*Primary Examiner*—Jerome D. Goldberg
*Attorney, Agent, or Firm*—Kenneth J. Dow

[57] ABSTRACT

Organic-platinum complexes useful as anti-cancer agents in the treatment of tumors sensitive to the subject compounds are described.

12 Claims, No Drawings

(2,2-BIS(AMINOMETHYL)-1,3-PROPRANEDIOL-N,N')PLATINUM COMPLEXES

CROSS REFERENCE TO RELATED APPLICATION

This application is a continuation-in-part of our co-pending application Ser. No. 06/825,023, filed Jan. 31, 1986 now U.S. Pat. No. 4,760,157.

SUMMARY OF THE INVENTION

This invention is concerned with a method of treating platinum complex sensitive tumors in warm-blooded animals by administering to them new organic compounds of the formulae:

$$\begin{array}{c}HOCH_2 \\ \\ HOCH_2\end{array} C \begin{array}{c}CH_2NH_2 \\ \\ CH_2NH_2\end{array} Pt \begin{array}{c}L \\ \\ L\end{array},$$

and $$\begin{array}{c}HOCH_2 \\ \\ HOCH_2\end{array} C \begin{array}{c}CH_2NH_2 \\ \\ CH_2NH_2\end{array} \begin{array}{c}X \\ | \\ Pt \\ | \\ X\end{array} \begin{array}{c}L \\ \\ L\end{array},$$

wherein L and L' are selected from the group consisting of halide, nitrate, sulfate and a monobasic carboxylate such as acetate or hydroxy acetate or L and L' taken together may be a dibasic carboxylate selected from the group consisting of

[structures shown]

oxalic acid, methylmalonic acid, succinic acid and tartronic acid, or L and L' taken together may be a tribasic carboxylate selected from the group consisting of

[structures shown]

and

[structure shown]

or L and L' taken together is ascorbic acid; and X is selected from the group consisting of halogen and hydroxy.

The compounds of this invention may be prepared according to the following reaction scheme:

[reaction scheme showing compounds (1), (2), (3), (4) with NaN₃, H₂, K₂PtCl₄ reagents]

-continued

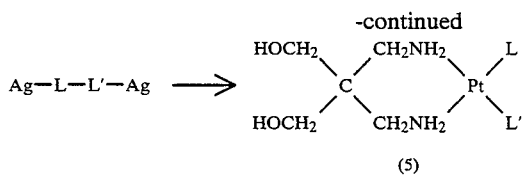

(5)

In accordance with the above reaction scheme, 2,2-dibromomethyl-1,3-propanediol (1) is reacted with sodium azide in dimethylformamide at 110°–120° C. for 20 hours giving 2,2-bis(azidomethyl)-1,3-propanediol (2) which is then catalytically reduced to 2,2-bis(aminomethyl)-1,3-propanediol (3). This compound is then reacted with potassium tetrachloroplatinate to give the dichloroplatinum product (4) which may further be reacted with the disilver salt of a dibasic organic acid to provide the products where L and L' taken together are as hereinbefore described.

Alternatively, platinum derivative (4) may be reacted with silver nitrate to give derivative (6) which is then reacted with a dicarboxylic acid (H-L-L'-H) in the presence of two equivalents of sodium hydroxide to give the product (5).

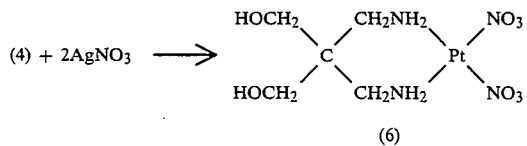

(6)

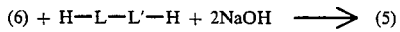

The compounds of this invention where X is halogen or hydroxy may be prepared by reacting the product 4 with chlorine gas in dilute hydrochloric acid, giving 7 or by reacting products 4 to 5 with hydrogen peroxide, giving 8.

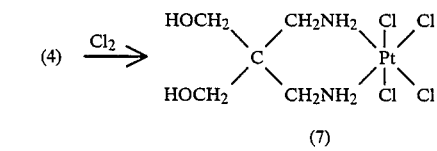

(7)

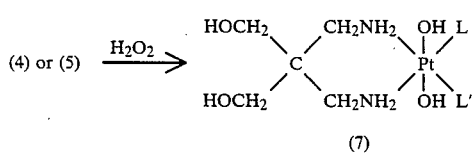

(7)

Lymphocytic Leukemia P388 Test

The animals used were BDF/1 mice, all of one sex, weighing a minimum of 18 g and all within a 3 g weight range. There were 5 to 6 animals per test group. The tumor transplant was by intraperitoneal injection of 0.5 ml of dilute ascitic fluid containing $10^6$ cells of lymphocytic leukemia P388. The test compounds were administered intraperitoneally on days 1, 5 and 9 relative to tumor inoculation, at various doses. The animals were weighed and the survivors recorded on a regular basis for 30 days. The median survival time and the ratio of survival time for treated (T)/control (C) animals were calculated. The positive control compound was Cisplatin. The results of this test with representative compounds of this invention appear in Table I.

TABLE I

| Lymphocytic Leukemia P388 Test | | | |
|---|---|---|---|
| Compound | Dose (mg/kg) | Median Survival (Days) | T/C × 100 (%) |
| [2,2-bis(aminomethyl)-1,3-propanediol-N,N']dichloroplatinum | 3.1 | 14 | 127 |
| | 1.5 | 19 | 173 |
| Control | — | 11 | — |
| Cisplatin | 1 | 15 | 136 |
| | 0.2 | 14.5 | 132 |
| | 0.06 | 10 | 91 |
| [2,2-bis(aminomethyl)-1,3-propanediol-N,N'][propanedioato-(2-)-$O^1,O^3$]platinum | 6.2 | 15 | 136 |
| | 3.1 | 22.5 | 205 |
| | 1.5 | 21.5 | 195 |
| Control | — | 11 | — |
| Cisplatin | 5 | 23 | 209 |
| | 2.5 | 28 | 255 |
| | 1.25 | 24 | 218 |
| [2,2-bis(aminomethyl)-1,3-propanediol-N,N'][2,2'-oxybis-[acetato]](2-)-$O^1,O^{1'}$]platinum | 6.2 | 21.5 | 195 |
| | 3.1 | 14.5 | 132 |
| | 1.5 | 16.5 | 150 |
| Control | — | 11 | — |
| Cisplatin | 5 | 23 | 209 |
| | 2.5 | 28 | 255 |
| | 1.25 | 24 | 218 |
| [2,2-bis(aminomethyl)-1,3-propanediol-N,N'][[1,1'-cyclobutanedicarboxylato](2-)-$O^1,O^{1'}$]-platinum | 6.2 | 18 | 164 |
| | 3.1 | 23.5 | 214 |
| | 1.5 | 20 | 182 |
| Control | — | 11 | — |
| Cisplatin | 5 | 23 | 209 |
| | 2.5 | 28 | 255 |
| | 1.25 | 24 | 218 |
| [2,2-bis(aminomethyl)-1,3-propanediol-N,N'][pentanedioato-(2-)-$O^1,O^5$]platinum | 25 | 17 | 155 |
| | 12.5 | 20.5 | 186 |
| | 6.2 | 18 | 164 |
| | 3.1 | 16.5 | 150 |
| | 1.5 | 13 | 118 |
| Control | — | 11 | — |
| Cisplatin | 5 | 23 | 209 |
| | 2.5 | 28 | 255 |
| | 1.25 | 24 | 218 |
| [2,2-bis(aminomethyl)-1,3-propanediol-N,N'][3,4-dihydroxy-3-cyclobutene-1,2-dionato(2-)-$O^3,O^4$]platinum | 6.2 | 12.5 | 125 |
| | 3.1 | 20 | 200 |
| | 1.5 | 19 | 190 |
| Control | — | 10 | — |
| Cisplatin | 1.25 | 25.5 | 255 |
| | 0.62 | 20.5 | 205 |
| [2,2-bis(aminomethyl)-1,3-propanediol-N,N']bis[hydroxyacetato(1-)-$O^1$]platinum | 3.1 | 24.5 | 245 |
| | 1.5 | 25.5 | 255 |
| Control | — | 10 | — |
| Cisplatin | 2 | 15.5 | 155 |
| | 1 | 22.7 | 227 |
| [2,2-bis(aminomethyl)-1,3-propanediol-N,N'][1,1,2-ethanetricarboxylato](2-)-$O^1,O^{1'}$]platinum | 25 | 18 | 180 |
| | 12.5 | 19 | 190 |
| | 6.2 | 16.5 | 165 |
| | 3.1 | 14 | 140 |
| Control | — | 10 | — |
| Cisplatin | 2 | 24 | 240 |
| | 1 | 22 | 220 |

Melanotic Melanoma B16

The animals used were C57BC/6 mice, all of the same sex, weighing a minimum of 17 g and all within a 3 g weight range. There were 10 animals per test group. A 1 g portion of melanotic melanoma $B_{16}$ tumor was homogenized in 10 ml of cold balanced salt solution and a 0.5 ml aliquot of the homogenate was implanted intraperitoneally into each of the test mice. The test compounds were administered intraperitoneally on days 1 through 9, relative to tumor inoculation, at various doses. The animals were weighed and survivors recorded on a regular basis for 60 days. The median survival time for treated (T)/control (C) animals were calculated. The positive control compound was Cisplatin. The results of this test appear in Table II.

TABLE II

| Melanotic Melanoma B16 Test | | | |
|---|---|---|---|
| Compound | Dose (mg/kg) | Median Survival (Days) | T/C × 100 (%) |
| [2,2-bis(aminomethyl)-1,3-propanediol-N,N']dichloroplatinum | 0.1 | 28 | 147 |
| Control | — | 19 | — |
| Cisplatin | 0.4 | 29.5 | 155 |
|  | 0.2 | 25.5 | 134 |
|  | 0.1 | 20.5 | 108 |
| [2,2-bis(aminomethyl)-1,3-propanediol-N,N'][propanedioato-(2-)-$O^1,O^3$]platinum | 1.5 | 26 | 137 |
|  | 0.8 | 37 | 195 |
|  | 0.4 | 30.5 | 161 |
|  | 0.2 | 29.5 | 155 |
| Control | — | 19 | — |
| Cisplatin | 0.4 | 29.5 | 155 |
|  | 0.2 | 25.5 | 134 |
|  | 0.1 | 20.5 | 108 |
| [2,2-bis(aminomethyl)1,3-propanediol-N,N'][[2,2'-oxybis-[acetato]](2-)-$O^1,O^1$]platinum | 1.5 | 28.5 | 150 |
|  | 0.8 | 27 | 142 |
|  | 0.4 | 20 | 105 |
|  | 0.2 | 20.5 | 108 |
| Control | — | 19 | — |
| Cisplatin | 0.4 | 29.5 | 155 |
|  | 0.2 | 25.5 | 134 |
|  | 0.1 | 20.5 | 108 |
| [2,2-bis(aminomethyl)-1,3-propanediol-N,N'][[1,1'-cyclobutanedicarboxylato](2-)-$O^1,O^1$]platinum | 0.8 | 38.5 | 203 |
|  | 0.4 | 27.5 | 145 |
|  | 0.2 | 27 | 142 |
| Control | — | 19 | — |
| Cisplatin | 0.4 | 29.5 | 155 |
|  | 0.2 | 25.5 | 134 |
|  | 0.1 | 20.5 | 108 |
| [2,2-bis(aminomethyl)-1,3-propanediol-N,N'][3,4-dihydroxy-3-cyclobutene-1,2-dionato(2-)-$O^3,O^4$]platinum | 1.5 | 19.5 | 103 |
|  | 0.8 | 29 | 153 |
|  | 0.4 | 23.5 | 124 |
|  | 0.2 | 22.5 | 116 |
| Control | — | 19 | — |
| Cisplatin | 0.4 | 29.5 | 155 |
|  | 0.2 | 25.5 | 134 |
|  | 0.1 | 20.5 | 108 |

Colon 26 Adenocarcinoma Test

The animals used were Balb/C mice all of one sex, weighing a minimum of 17 g and all within a 3 g weight range. There were 5 or 6 mice per test group with three groups of 5 or 6 animals used as untreated controls for each test. The tumor implant was by intraperitoneal (or subcutaneous) injection of 0.5 ml of a 2% Colon 26 tumor brei in Eagle's MEM medium containing antibiotics. The test compounds were administered intraperitoneally on days 1, 5 and 9 (relative to tumor implant doses). The mice were weighed and deaths recorded on a regular basis for 30 days. The median survival times and the ratio of survival time for treated (T)/control (C) animals were calculated. The positive control compound was Cisplatin. The results of this test on representative compounds of this invention appear in Table III.

TABLE III

| Colon 26 Adenocarcinoma Test | | | |
|---|---|---|---|
| Compound | Dose (mg/kg) | Median Survival (Days) | T/C × 100 (%) |
| [2,2-bis(aminomethyl)-1,3-propanediol-N,N']dichloroplatinum | 1.5 | 19 | 123 |
|  | 0.8 | 15.5 | 100 |
|  | 0.4 | 16 | 103 |
| Control | — | 15.5 | — |
| Cisplatin | 1 | 27.5 | 177 |
|  | 0.5 | 16.5 | 106 |
|  | 0.25 | 16 | 103 |
| [2,2-bis(aminomethyl)-1,3-propanediol-N,N'][propanedioato-(2-)-$O^1,O^3$]platinum | 3 | 25 | 161 |
|  | 1.5 | 18.5 | 119 |
| Control | — | 15.5 | — |
| Cisplatin | 1 | 27.5 | 177 |
|  | 0.5 | 16.5 | 106 |
|  | 0.25 | 16 | 103 |
| [2,2-bis(aminomethyl)-1,3-propanediol-N,N'][[2,2'-oxybis-[acetato]](2-)-$O^1,O^1$]platinum | 1.5 | 16.5 | 106 |
|  | 0.8 | 16 | 103 |
| Control | — | 15.5 | — |
| Cisplatin | 1 | 27.5 | 177 |
|  | 0.5 | 16.5 | 106 |
|  | 0.25 | 16 | 103 |
| [2,2-bis(aminomethyl)-1,3-propanediol-N,N'][[1,1'-cyclobutanedicarboxylato](2-)-$O^1,O^1$]platinum | 6 | 24 | 155 |
|  | 3 | 21 | 135 |
|  | 1.5 | 20 | 129 |
|  | 0.8 | 18.5 | 119 |
| Control | — | 15.5 | — |
| Cisplatin | 1 | 27.5 | 177 |
|  | 0.5 | 16.5 | 106 |
|  | 0.25 | 16 | 103 |
| [2,2-bis(aminomethyl-1,3-propanediol-N,N'][3,4-dihydroxy-3-cyclobutene-1,2-dionato(2-)-$O^3,O^4$]platinum | 1.5 | 19 | 123 |
|  | 0.8 | 17.5 | 113 |
| Control | — | 15.5 | — |
| Cisplatin | 1 | 27.5 | 177 |
|  | 0.5 | 16.5 | 106 |
|  | 0.25 | 16 | 103 |

Lymphocytic Leukemia L1210 Test

The animals used were $BDF_1$ of $CD_2F_1$ mice, all of one sex, weighing a minimum of 17 g and all within a 3 g. weight range. There were 6 mice in each test group and 18 in control groups. The tumor transplant was by intraperitoneal injection of 0.5 ml of lymphocytic leukemia L1210 at a concentration of $10^5$ cells per mouse. The test compounds were administered on days 1, 5 and 9 (relative to tumor inoculation) at various doses. The mice were weighed and survivors recorded on a regular basis for 30 days. The median survival time and the ratio of survival time for treated (T)/control (C) animals were calculated. The positive control compound was Cisplatin given intraperitoneally at the indicated doses. The results of this test on representative compounds of this invention appear in Table IV.

TABLE IV

| Lymphocytic Leukemia L1210 Test | | | |
|---|---|---|---|
| Compound | Dose (mg/kg) | Median Survival (Days) | T/C × 100 (%) |
| [2,2-bis(aminomethyl)-1,3-propanediol-N,N']dichloroplatinum | 1.5 | 12.5 | 139 |
|  | 0.8 | 10.5 | 117 |
| Control | — | 9 | — |
| Cisplatin | 2.5 | 10 | 111 |
|  | 1.25 | 11 | 122 |
| [2,2-bis(aminomethyl)-1,3-propanediol-N,N'][propanedioato-(2-)-$O^1,O^3$]platinum | 6.2 | 11 | 138 |
|  | 3.1 | 9.5 | 119 |
|  | 1.5 | 9 | 113 |
|  | 0.8 | 9 | 113 |
| Control | — | 8 | — |

TABLE IV-continued

Lymphocytic Leukemia L1210 Test

| Compound | Dose (mg/kg) | Median Survival (Days) | T/C × 100 (%) |
|---|---|---|---|
| Cisplatin | 2.5 | 14 | 175 |
| [2,2-bis(aminomethyl)-1,3-pro- | 6.2 | 8 | 100 |
| panediol-N,N'][[2,2'-oxybis- | 3.1 | 9 | 113 |
| [acetato]](2-)-0$^1$,0$^1$]platinum | 1.5 | 9 | 113 |
|  | 0.8 | 9 | 113 |
| Control | — | 8 | — |
| Cisplatin | 2.5 | 14 | 175 |
| [2,2-bis(aminomethyl)-1,3-pro- | 6.2 | 8.5 | 106 |
| panediol-N,N'][[1,1'-cyclo- | 3.1 | 11 | 138 |
| butanedicarboxylato](2-)-0$^1$,0$^1$]- | 1.5 | 9 | 113 |
| platinum | 0.8 | 9 | 113 |
| Control | — | 8 | — |
| Cisplatin | 2.5 | 14 | 175 |
| [2,2-bis(aminomethyl)-1,3-prop- | 3.1 | 8.5 | 94 |
| panediol-N,N'][3,4-dihydroxy-3- | 1.5 | 11.5 | 128 |
| cyclobutene-1,2-dionato(2-)- | 0.8 | 11 | 122 |
| 0$^3$,0$^4$]platinum |  |  |  |
| Control | — | 9 | — |
| Cisplatin | 2.5 | 14 | 156 |
|  | 1.25 | 12.5 | 139 |

M5076 Sarcoma

The M5076 reticular cell Sarcoma is propagated as subcutaneous (sc) implants in C57B2/6 female mice. In the assays for antitumor activity, BDF$_1$ mice of either sex were inoculated intraperitoneally (ip) with 0.5 ml of a 10% tumor brei. Test compounds were administered ip on days 1, 5, 9, 13 and 17 relative to tumor inoculation on day zero. The median survival time in days was determined for each drug dose used on day 60 and the ratio of survival time for treated (T)/control (C) animals were calculated.

The results of this test on representative compounds of this invention appear in Table V, compared to the results obtained with Cisplatin.

TABLE V

M5076 Sarcoma Test

| Compound | Dose (mg/kg) | Median Survival (Days) | T/C × 100 (%) |
|---|---|---|---|
| [2,2-bis(aminomethyl)-1,3-pro- | 0.8 | >59.5 | >238 |
| panediol-N,N']dichloroplatinum | 0.4 | >60 | >240 |
|  | 0.2 | 49 | 196 |
| Control | — | 25 | — |
| Cisplatin | 1.6 | 56 | 224 |
|  | 0.8 | 50 | 200 |
| [2,2-bis(aminomethyl)-1,3-pro- | 1.5 | 54 | 216 |
| propanediol-N,N'][propane- | 0.8 | 49.5 | 198 |
| dioato(2-)-0$^1$,0$^3$]platinum | 0.4 | 38.5 | 154 |
| Control | — | 25 | — |
| Cisplatin | 1.6 | 56 | 224 |
|  | 0.8 | 50 | 200 |
| [2,2-bis(aminomethyl)-1,3- | 3 | 48.2 | 194 |
| propanediol-N,N'][[2,2'-oxybis- | 1.5 | 40 | 160 |
| [acetato]](2-)-0$^1$,0$^1$]platinum | 0.8 | 33.5 | 134 |
|  | 0.4 | 34 | 136 |
| Control | — | 25 | — |
| Cisplatin | 1.6 | 56 | 224 |
|  | 0.8 | 50 | 200 |
| [2,2-bis(aminomethyl)-1,3- | 3 | >60 | >240 |
| propanediol-N,N'][[1,1-cyclobut- | 1.5 | >58 | >232 |
| anedicarboxylato](2-)-0$^1$,0$^1$]- | 0.8 | 50.5 | 202 |
| platinum | 0.4 | 42 | 168 |
| Control | — | 25 | — |
| Cisplatin | 1.6 | 56 | 224 |
|  | 0.8 | 50 | 200 |
| [2,2-bis(aminomethyl)-1,3- | 3 | >60 | >240 |
| propanediol-N,N'][3,4-dihydroxy- | 1.5 | 47 | 188 |
| 3-cyclobutene-1,2-dionato(2-)- | 0.8 | 42 | 168 |
| 0$^3$,0$^4$]platinum | 0.4 | 40 | 160 |
| Control | — | 25 | — |
| Cisplatin | 1.6 | 56 | 224 |
|  | 0.8 | 50 | 200 |

This aspect of the invention includes novel compositions of matter and the method of inducing the regression and/or palliation of platinum complex sensitive leukemia and related cancers in mammals using the novel compounds of this invention when administered in amounts ranging from about 1 mg to about 1.2 g per square meter of body surface area per day. The interrelationship of dosages for animals of various sizes and species and humans (based on mg/m$^2$ of surface area) is described by Freireich, E. J. et al., Quantitative Comparison of Toxicity of Anticancer Agents in Mouse, Rat, Hamster, Dog, Monkey and Man. Cancer Chemother. Rep., 50, No. 4, 219-244, May 1966. A preferred dosage regimen for optimum results would be from about 3 mg/m$^2$/day to about 200 mg/m$^2$/day, and such dosage units are employed that a total of from about 5 mg to about 360 mg of the active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The active compound may be administered by the intravenous, intramuscular or subcutaneous routes.

The active compounds may be administered parenterally. Solutions or dispersions of the active compound can be prepared in water, suitably mixed with a surfactant such as hydroxypropylcellulose. Dispersions can also be prepared in glycerol, liquid polyethylene glycols, and mixtures thereof in oils. Under ordinary conditions of storage and use these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol, liquid polyethylene glycol), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be obtained by the use in the compositions of agents which delay absorption, for example, aluminum monostearate and gelatin. Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatable with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subject to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 2 mg to about 2 g, with from about 5 to about 360 mg being preferred. Expressed in proportions, the active compound is generally present in from about 2 to about 100 mg/ml of carrier. In the case of compositions containing supplementary active ingredients, the dosages are determined by reference to the usual dose and manner of administration of the said ingredients.

Regression and palliation of cancers are attained, for example, using intraperitoneal administration. A single intravenous dosage or repeated daily dosages can be administered. Daily dosages up to about 5 to 10 days are often sufficient. It is also possible to dispense one daily dosage or one dose on alternate or less frequent days. As can be seen from the dosage regimens, the amount of principal active ingredient administered is a sufficient amount to aid regression and palliation of the leukemia or the like, in the absence of excessive deleterious side effects of a cytotoxic nature to the host harboring the cancer. As used herein, cancer disease means any form of cancer sensitive to the subject compounds including blood malignancies such as leukemia, as well as other solid and non-solid malignancies such as the melanocarcinomas, lung carcinomas and mammary tumors. By regression and palliation is meant arresting or retarding the growth of the tumor or other manifestation of the disease compared to the course of the disease in the absence of treatment. This invention will be described in greater detail in conjuction with the following, non-limiting, specific examples.

EXAMPLE 1

[2,2-Bis(aminomethyl)-1,3-propanediol-N,N']dichloroplatinum

The compound 2,2-dibromomethyl-1,3-propanediol was prepared by the method M. Saivier (et al), Can. J. Chem; 44, 1599 (1966).

A mixture of 13.1 g of 2,2-dibromomethyl-1,3-propanediol, 6.5 g of sodium azide and 750 ml of dimethylformamide was stirred and heated at 110°–120° C. for 20 hours, then clarified and the filtrate evaporated. The residue was extracted three times with dichloromethane. The extracts were combined and evaporated, giving 13.65 g of 2,2-bis(azidomethyl)-1,3-propanediol, compound with dimethylformamide.

A 13 g portion of the above azido derivative was reduced with 0.1 g of platinum dioxide in ethanol, using 50 lbs. of hydrogen pressure for 20 hours. The mixture was then filtered and the filtrate concentrated to dryness, giving 9.34 g of 2,2-bis(aminomethyl)-1,3-propanediol as a pale yellow oil.

A mixture of 1.34 g of 2,2-bis(aminomethyl)-1,3-propanediol, 4.15 g of potassium dichloroplatinate and 22 ml of water was stirred for 2 hours, then cooled, the solid collected and washed three times with cold water. This solid was recrystallized from 60 ml of hot water, giving 890 mg of the desired product as beige crystals, mp 223°–225° C. (dec.).

EXAMPLE 2

[2,2-Bis(aminomethyl)-1,3-propanediol-N,N'][propanedioato(2-)-$O^1$, $O^3$]platinum A mixture of 0.4 g of [2,2-bis(aminomethyl)1,3-propanediol-N,N']dichloroplatinum and 0.32 g of the disilver salt of malonic acid in water was stirred in the dark overnight and then filtered. The filtrate was concentrated to dryness, giving 0.39 g of the desired product as colorless crystals, mp 230°–233° C. (dec.).

EXAMPLE 3

[2,2-Bis(aminomethyl)-1,3-propanediol-N,N'][[2,2-oxybis[acetato]](2-)$O^1$, $O^1$]platinum A mixture of 0.8 g of [2,2-bis(aminomethyl)1,3-propanediol-N,N']dichloroplatinum and 0.696 g of the disilver salt of diglycolic acid in 50 ml of water was stirred in the dark overnight and then filtered. The filtrate was evaporated to dryness, giving 0.7 g of the desired product as a beige glass, mp 193°–195° C. (dec.).

EXAMPLE 4

[2,2-Bis(aminomethyl)-1,3-propanediol-N,N'][[1,1'-cyclobutanedicarboxylato](2-)$O^1,O^1$]platinum A mixture of 0.8 g of [2,2-bis(aminomethyl)-1,3-propanediol-N,N']dichloroplatinum and 0.78 g of the disilver salt of 1,1-cyclobutane dicarboxylic acid in 50 ml of water was stirred in the dark overnight and then filtered. The filtrate was evaporated to dryness, giving 0.72 g of the desired product as a beige powder, mp 202°–205° C. (dec.).

EXAMPLE 5

[2,2-Bis(aminomethyl)-1,3-propanediol-N,N'][pentanedioato(2-)O¹, O⁵]platinum

A mixture of 0.4 g of [2,2-bis(aminomethyl)1,3-propanediol-N,N']dichloroplatinum and 0.346 g of the disilver salt of glutaric acid in 30 ml of water was stirred in the dark overnight and then filtered. The filtrate was evaporated to dryness, giving 0.45 g of the desired product as a colorless glass, mp 175°–180° C. (dec.).

EXAMPLE 6

[2,2-Bis(aminomethyl)-1,3-propanediol-N,N'][3,4-dihydroxy-3-cyclobutene-1,2-dionato(2-)-O³, O⁴]platinum A 0.52 g portion of [2,2-bis(aminomethyl)1,3-propanediol-N,N']dichloroplatinum in 45 ml of water was treated with 0.426 g of the disilver salt of 3,4-dihydroxy-3-cyclobutene-1,2-dione. This mixture was stirred in the dark for 16 hours and then filtered. The filtrate was evaporated to dryness, giving 0.51 g of the desired product as a glass, mp 170°–180° C. (dec.).

EXAMPLE 7

[2,2-Bis(aminomethyl)-1,3-propanediol-N,N'][[2,2'-sulfonylbis[acetato]](2-)-O¹, O¹]platinum A mixture of 0.8 g of [2,2-bis(aminomethyl)1,3-propanediol-N,N')dichloroplatinum and 0.792 g of the disilver salt of sulfonyldiacetic acid in 50 ml of water was stirred in the dark overnight and then filtered. The filtrate was evaporated to dryness, giving 0.73 g of the desired product as a glass, mp 180°–185° C. (dec.).

EXAMPLE 8

[2,2-Bis(aminomethyl)-1,3-propanediol-N,N']bis[hydroxyacetato(1-)-O¹]platinum

A mixture of 0.8 g of [2,2-bis(aminomethyl)-1,3-propanediol-N,N']dichloroplatinum, 0.73 g of the silver salt of hydroxyacetic acid and 125 ml of water was stirred overnight in the dark and then filtered through diatomaceous earth. The filtrate was allowed to stand overnight and then stripped to dryness. The residue was slurried with ethanol and the solid collected and dried, giving 0.39 g of the desired product, mp 185°–187° C. (dec.).

EXAMPLE 9

[2,2-Bis(aminomethyl)-1,3-propanediol-N,N'][1,1,2-ethanetricarboxylato(2-)-O¹,O¹]platinum A mixture of 0.8 g of [2,2-bis(aminomethyl)-1,3-propanediol-N,N']dichloroplatinum and 0.68 g of silver nitrate in water was stirred overnight and then filtered through diatomaceous earth. The filtrate was treated with a solution of 0.324 g of 1,1,2-ethanetricarboxylic acid in 5 ml of water and 4 ml of 1N sodium hydroxide. This mixture was allowed to stand for 8 hours and was then filtered. The filtrate was allowed to stand overnight in the cold and was then filtered. This filtrate was concentrated, treated with an equal volume of methanol and refrigerated overnight. The resulting solid was collected and washed with methanol giving 0.27 g of the desired product, mp 215°–220° C. (dec.).

EXAMPLE 10

[2,2-Bis(aminomethyl)-1,3-propanediol-N,N']tetrachloroplatinum

A 1.8 g portion of [2,2-bis(aminomethyl)-1,3-propanediol-N,N']dichloroplatinum is stirred in 40 ml of 0.5N hydrochloric acid and a slow stream of chlorine gas is bubbled through the reaction mixture. Within a few minutes a clear solution is obtained. Bubbling of chlorine gas is continued for 2 hours. Nitrogen is bubbled through to remove chlorine gas and the solution evaporated to dryness in vacuo. The yellow solid is taken up in 250 ml of methanol and the solution is filtered. The filtrate is evaporated to give 1.0 g of the desired product as yellow crystals.

EXAMPLE 11

[2,2-Bis(aminomethyl)-1,3-propanediol-N,N'][1,1'-cyclobutanedicarboxylato(2-)O¹,O¹]dihydroxyplatinum A 1.2 g portion of [2,2-bis(aminomethyl)-1,3-propanediol-N,N'][1,1'-cyclobutanedicarboxylato](2-)-O¹,O¹]platinum is suspended in 5 ml of distilled water. A 25 ml portion of 30% hydrogen peroxide is added. Stirring is carried out during 0.5 hour at room temperature, thereafter one hour under reflux. The suspension is cooled and the solid substance is filtered washed with water and dried under reduced pressure, giving 0.6 g of the desired product.

EXAMPLE 12

[2,2-Bis(aminomethyl)-1,3-propanediol-N,N']-[L-threo-3-hexulosonato(2-)-C²,O⁵-gamma-lactone]platinum To a suspension of 400 mg of [2,2-bis(aminomethyl)-1,3-propanediol-N,N']dichloroplatinum in 10 ml of water was added 338 mg of silver nitrate. The mixture was stirred for 2 hours and then filtered. To the filtrate was added 198 mg of sodium ascorbate. This mixture was stirred for 2 hours, then added to 70 ml of ethanol, stirred one additional hour and evaporated to dryness, giving 300 mg of the desired product.

EXAMPLE 13

[2,2-Bis(aminomethyl)-1,3-propanediol-N,N']-tetrachloroplatinum

Chlorine gas was bubbled into a mixture of 0.5 g. of [2,2-bis(aminomethyl)-1,3-propanediol-N,N']dichloroplatinum and 50 ml of 0.5N hydrochloric acid for 2 hours at 90° C. The mixture was then cooled, nitrogen was passed through the solution to remove excess chlorine and the solution was evaporated to dryness, giving 557 mg of the desired product.

What is claimed is:

1. A method of treating a warm blooded animal afflicted with tumor cells sensitive to a compound of the formula:

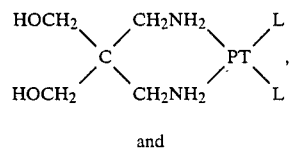

and

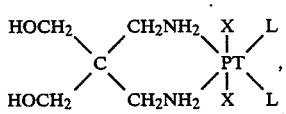

wherein L and L' are selected from the group consisting of halide, nitrate, sulfate and a monobasic carboxylate such as acetate or hydroxy acetate or L and L' taken together are a dibasic carboxylate selected from the group consisting of

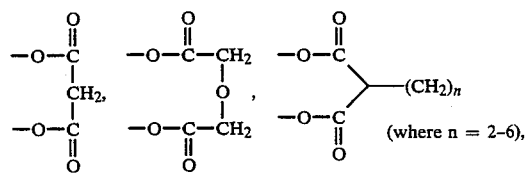

(where n = 2-6),

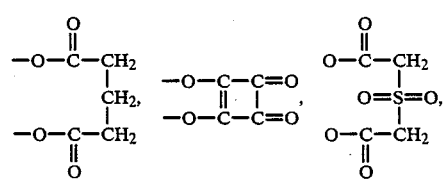

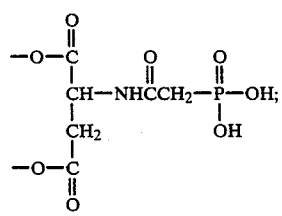

oxalic acid, methylmalonic acid, succinic acid and tartronic acid, or L and L' taken together are a tribasic carboxylate selected from the group consisting of

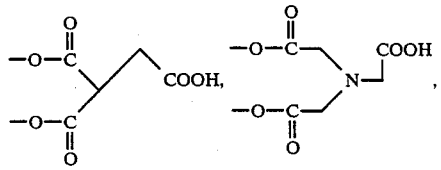

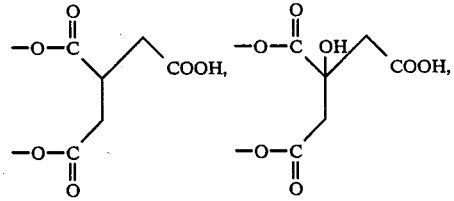

and

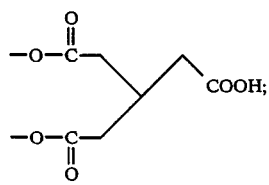

or L and L' taken together is ascorbic acid and x is selected from the group consisting of halogen and hydroxy; which comprises parenterally administering to said animal an oncolytic amount of said compound of the above formula.

2. The method according to claim 1 wherein the compound is [2,2-bis(aminomethyl)-1,3-propanediol-N,N']dichloroplatinum.

3. The method according to claim 1 wherein the compound is [2,2-bis(aminomethyl)-1,3-propanediol-N,N'][propanedioato-(2-)-O',O$^3$]platinum.

4. The method according to claim 1 wherein the compound is [2,-2-bis(aminomethyl)-1,3-propanediol-N,N'][2,2'-oxybis-[acetato]](2-)-O$^1$,O$^1$]platinum.

5. The method according to claim 1 wherein the compound is [2,2-bis(aminomethyl)-1,3-propanediol-N,N'][[1,1'-cyclobutane-dicarboxylato](2-)-O$^1$]platinum.

6. The method according to claim wherein the compound is [2,2-bis(aminomethyl)-1,3-propanediol-N,N'][pentanedioato(2-)-O$^1$, O$^5$]platinum.

7. The method according to claim 1 wherein the compound is [2,2-bis(aminomethyl)-1,3-propanediol-N,N'][3,4-dihydroxy-3-cyclobutene-1,2-dionato(2-)-O$^3$,O$^4$]platinum.

8. The method according to claim 1 wherein the compound is [2,2-bis(aminomethyl)-1,3-propanediol-N,N'][[2,2'-sulfonylbis [acetato]](2-)-O$^1$,O$^1$]platinum.

9. The method according to claim 1 wherein the compound is [2,2-bis (aminomethyl)-1,3-propanediol-N,N']bis[hydroxyacetato(1-)-O$^1$]platinum.

10. The method according to claim 1 wherein the compound is [2,2-bis-(aminomethyl)-1,3-propanediol-N,N'][1,1,2-ethanetricarboxylato(2-)-O$^1$,O$^1$]platinum.

11. The method according to claim 1 wherein the compound is [2,2-bis-(aminomethyl)-1,3-propanediol-N,N') tetrachloroplatinum.

12. The method according to claim 1 wherein the compound is [2,2-dicarboxylato(2-)-O$^1$,O$^1$]dihydroxyplatinum.

* * * * *

UNITED STATES PATENT OFFICE
CERTIFICATE OF CORRECTION

Page 1 of 2

Patent No. 4,900,756          Dated February 13, 1990

Inventor(s) Ralph G. Child et al.

It is certified that error appears in the above-identified patent and that said Letters Patent is hereby corrected as shown below:

Cover page, in the Title, "PROPRANEDIOL" should be --PROPANEDIOL--.

Column 1, Line 1, "PROPRANEDIOL" should be --PROPANEDIOL--.

Column 1, Lines 35-40, the structure:

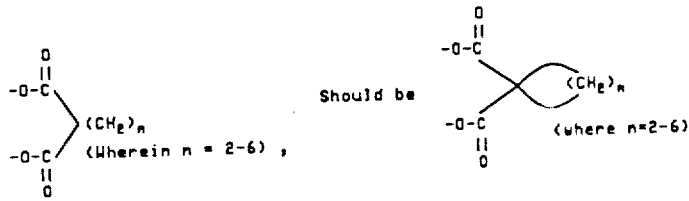

UNITED STATES PATENT AND TRADEMARK OFFICE
CERTIFICATE OF CORRECTION

PATENT NO. : 4,900,756

DATED : February 13, 1990

INVENTOR(S) : Ralph G. Child et al.

It is certified that error appears in the above-identified patent and that said Letters Patent is hereby corrected as shown below:

Column 13, lines 19-24, the structure:

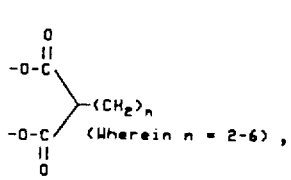 Should be 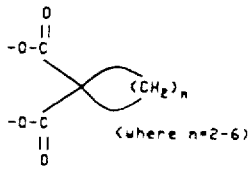

Signed and Sealed this

Ninth Day of July, 1991

*Attest:*

*Attesting Officer*

HARRY F. MANBECK, JR.

*Commissioner of Patents and Trademarks*